US00PP33046P2

(12) United States Plant Patent
Kobayashi

(10) Patent No.: US PP33,046 P2
(45) Date of Patent: May 11, 2021

(54) **NEW GUINEA *IMPATIENS* PLANT NAMED 'DONGIMAGMA'**

(50) Latin Name: *Impatiens hawkeri*
Varietal Denomination: Dongimagma

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,768

(22) Filed: Jun. 29, 2020

(51) Int. Cl.
*A01H 5/02* (2018.01)
*A01H 6/16* (2018.01)

(52) U.S. Cl.
USPC ..... Plt./318.6

(58) Field of Classification Search
USPC ..... Plt./318.6, 318.5, 318.4
CPC ... A01H 5/02; A01H 5/00; A01H 6/16; A01H 6/165; A01H 6/56
See application file for complete search history.

*Primary Examiner* — June Hwu
(74) *Attorney, Agent, or Firm* — C. Anne Whealy

(57) ABSTRACT

A new and distinct cultivar of *Impatiens* plant named 'Dongimagma' characterized by its upright to outwardly spreading and uniformly mounding plant habit; moderately vigorous growth habit; freely branching habit; glossy and dark green-colored leaves; freely flowering habit; large flowers with spatulate to cordate-shaped petals that are dark red purple in color; and good garden performance.

2 Drawing Sheets

Figure 1:
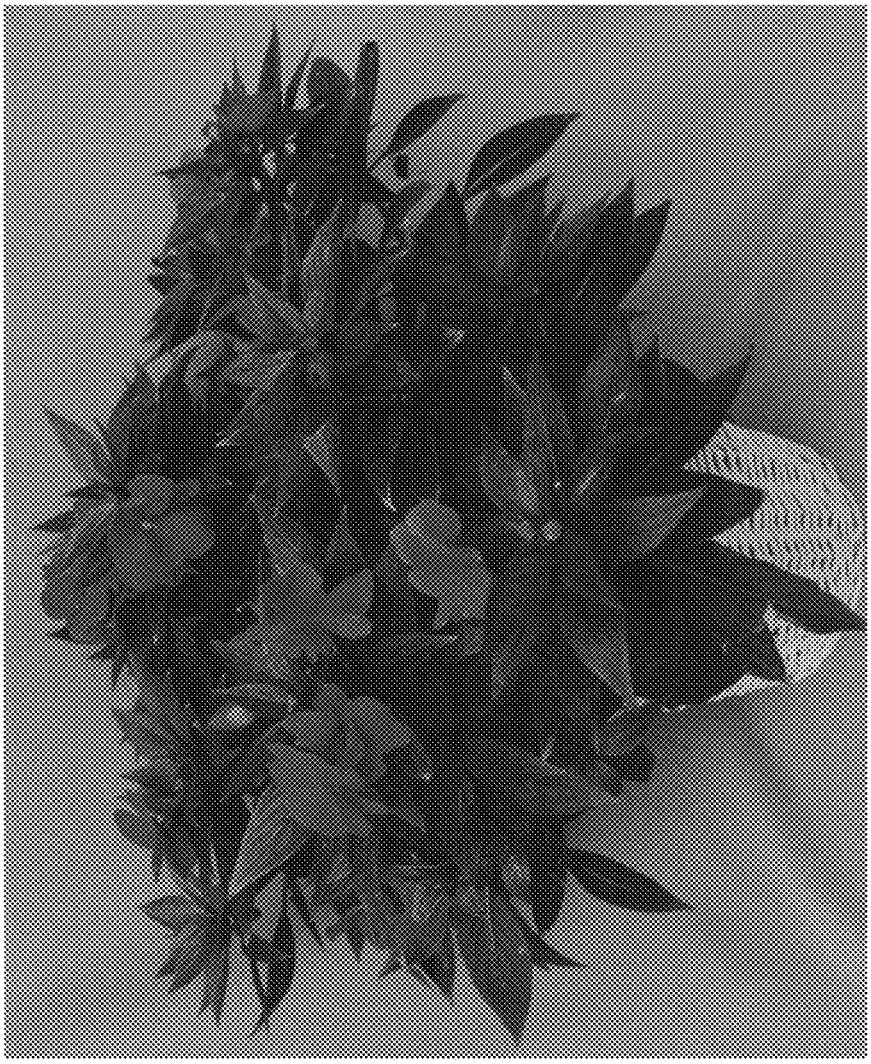

Botanical designation: *Impatiens hawkeri.*
Cultivar denomination: 'DONGIMAGMA'.

STATEMENT REGARDING PRIOR DISCLOSURES BY THE INVENTOR AND APPLICANT

The Inventor and Applicant assert that no sales, publications or advertisements relating to sales, offers for sale or public distribution occurred more than one year prior to the effective filing date of this application. Any information about the claimed plant would have been obtained from a direct or indirect disclosure from the Inventor and/or the Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known *as Impatiens hawkeri* and hereinafter referred to by the name 'Dongimagma'.

The new *Impatiens* plant is a product of a planned breeding program conducted by the Inventor in Koka, Ethiopia and Encinitas, Calif. The objective of the breeding program is to create new early and freely flowering New Guinea *Impatiens* plants with large attractive flowers and good garden performance.

The new *Impatiens* plant originated from a cross-pollination made by the Inventor in November, 2015 in Koka, Ethiopia of a proprietary selection of *Impatiens hawkeri* identified as code number NN13-008045-001, not patented, as the female, or seed, parent with *Impatiens hawkeri* 'Doimtatrure', disclosed in U.S. Plant Pat. No. 30,689, as the male, or pollen, parent. The new *Impatiens* plant was discovered and selected by the Inventor as a single flowering plant from within the progeny of the stated cross-pollination in a controlled greenhouse environment in Encinitas, Calif. in April, 2016.

Asexual reproduction of the new *Impatiens* plant by terminal vegetative cuttings in a controlled greenhouse environment in Rheinberg, Germany since June, 2016 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongimagma'. These characteristics in combination distinguish 'Dongimagma' as a new and distinct *Impatiens* plant:

1. Upright to outwardly spreading and uniformly mounding plant habit.
2. Moderately vigorous growth habit.
3. Freely branching habit.
4. Glossy and dark green-colored leaves.
5. Freely flowering habit.
6. Large flowers with spatulate to cordate-shaped petals that are dark red purple in color.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are not as vigorous as plants of the female parent selection.
2. Plants of the new *Impatiens* have larger flowers than plants of the female parent selection.
3. Flowers of plants of the new *Impatiens* are dark red purple in color whereas flowers of plants of the female parent selection are dark red in color.

Plants of the new *Impatiens* can be compared to plants of the male parent, 'Doimtatrure'. Plants of the new *Impatiens* differ primarily from plants of 'Doimtatrure' in flower color as plants of the new *Impatiens* have dark red purple-colored flowers whereas plants of 'Doimtatrure' have bright red-colored flowers. In addition, plants of the new *Impatiens* are slightly more vigorous than plants of 'Doimtatrure'.

Plants of the new *Impatiens* can be compared to plants of *Impatiens hawkeri* 'Doimmalaven', disclosed in U.S. Plant Pat. No. 30,744. In side-by-side comparisons, plants of the new *Impatiens* differ primarily from plants of 'Doimmalaven' in the following characteristics:

1. Plants of the new *Impatiens* have smaller flowers than plants of 'Doimmalaven'.
2. Flowers of plants of the new *Impatiens* are dark red purple in color whereas flowers of plants of 'Doimmalaven' are purple to red purple in color with white-colored centers.

Plants of the new *Impatiens* can also be compared to plants of *Impatiens hawkeri* 'Papete', disclosed in U.S. Plant Pat. No. 8,457. In side-by-side comparisons, plants of the new *Impatiens* differ primarily from plants of 'Papete' in the following characteristics:

1. Plants of the new *Impatiens* are more vigorous than and not as compact as plants of 'Papete'.
2. Plants of the new *Impatiens* have larger flowers than plants of 'Papete'.
3. Flowers of plants of the new *Impatiens* are dark red purple in color whereas flowers of plants of 'Papete' are purplish red in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1 of 2) is a side perspective view of a typical flowering plant of 'Dongimagma' grown in a container.

Figure 2:
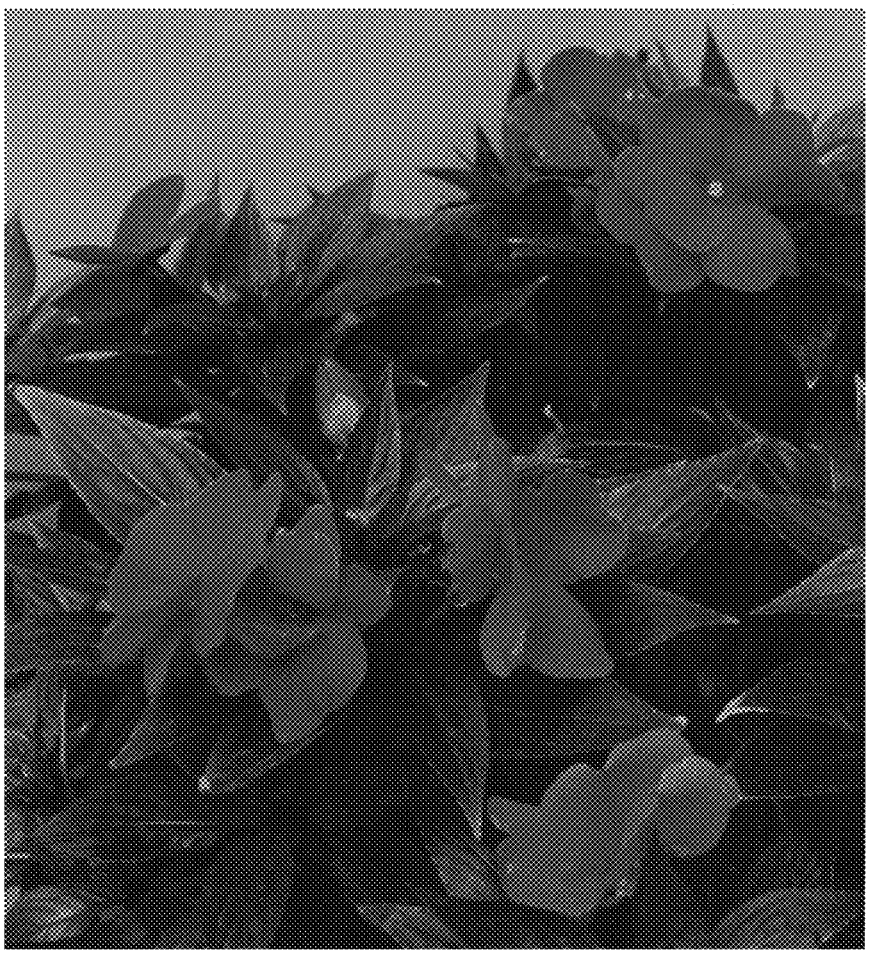

The photograph on the second sheet (FIG. 2 of 2) is a close-up view of a typical flowering plant of 'Dongimagma'.

DETAILED BOTANICAL DESCRIPTION

The aforementioned photographs and following observations, measurements and values describe plants grown during the summer and early autumn in 16.5-cm containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 4,500 to 5,500 lux. Plants were 17 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongimagma'.

Parentage:

*Female, or seed, parent.*—Proprietary selection of *Impatiens hawkeri* identified as code number NN13-008045-001, not patented.

*Male, or pollen, parent.*—*Impatiens hawkeri* 'Doimtatrure', disclosed in U.S. Plant Pat. No. 30,689.

Propagation:

*Type.*—By terminal vegetative cuttings.

*Time to initiate roots, summer and winter.*—About five to seven days at day temperatures about 27° C. and night temperatures about 20° C.

*Time to produce a rooted young plant, summer and winter.*—About three weeks at day temperatures about 27° C. and night temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to outwardly spreading and uniformly mounding plant habit; broad inverted triangle in overall shape; freely branching habit; bushy and dense appearance; moderately vigorous growth habit and moderate to rapid growth rate.

*Plant height.*—About 36 cm.

*Plant diameter.*—About 51 cm.

Lateral branch description:

*Branching habit.*—Freely branching with about five primary lateral branches each with multiple secondary branches.

*Length.*—About 33 cm.

*Diameter.*—About 1.5 cm.

*Internode length.*—About 8.5 cm.

*Strength.*—Strong, flexible.

*Aspect.*—Initially upright to outwardly spreading.

*Texture and luster.*—Smooth, glabrous; glossy.

*Color, developing.*—Close to 187A.

*Color, developed.*—Close to 148A strongly tinged with close to 187A.

Leaf description:

*Arrangement.*—Typically in whorls or opposite; simple.

*Length.*—About 10.5 cm.

*Width.*—About 4.5 cm.

*Shape.*—Elliptic to narrowly ovate.

*Apex.*—Acuminate.

*Base.*—Cuneate to attenuate.

*Margin.*—Serrate with ciliation.

*Texture and luster, upper surface.*—Smooth, glabrous; coriaceous; glossy.

*Texture and luster, lower surface.*—Smooth, glabrous; coriaceous; slightly glossy.

*Venation pattern.*—Pinnate; arcuate.

*Color.*—Developing leaves, upper surface: More green than 137A. Developing leaves, lower surface: Close to 137B to 137C. Fully expanded leaves, upper surface: Close to between 147A and N189A; midvein, proximally, close to 58A and distally, close to 144A; lateral venation, close to between 147A and N189A. Fully expanded leaves, lower surface: Close to 147B; midvein and lateral venation, close to 53A.

*Petiole length*.—About 4.25 cm.

*Petiole diameter*.—About 5 mm.

*Petiole texture and luster, upper and lower surfaces*.—Smooth, glabrous; glossy.

*Petiole color, upper surface*.—Close to 58A.

*Petiole color, lower surface*.—Close to 53A.

Flower description:

*Flower type and flowering habit*.—Large single axillary flowers that are rounded to slightly rectangular in shape; freely flowering habit, typically about three fully opened flowers and three to four flower buds per lateral branch; flowers are slightly cupped and positioned above and beyond the foliar plane, flowers typically face mostly upright.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about twelve weeks from unrooted cuttings.

*Flower buds*.—Length: About 1.5 cm. Diameter: About 1 cm. Shape: Ovoid. Texture and luster: Smooth, glabrous; somewhat glossy. Color: Close to N57C and N57A.

*Flower diameter*.—Large, about 6.8 cm by 6.4 cm.

*Flower depth*.—About 2.5 cm.

*Petals*.—Quantity and arrangement: Five per flower in a single whorl with one banner petal, two lateral petals and two lower petals. Length, banner petal: About 3.5 cm. Length, lateral petals: About 3.5 cm. Length, lower petals: About 3.5 cm. Width, banner petal: About 5.75 cm. Width, lateral petals: About 4 cm. Width, lower petals: About 4 cm. Shape, banner petals: Broadly spatulate to cordate. Shape, lateral and lower petals: Spatulate to cordate. Apex, all petals: Cordate. Base, all petals: Cuneate. Margin, all petals: Entire, not undulate. Texture and luster, all petals, upper surface: Smooth, glabrous; velvety; slightly glossy; iridescent. Texture and luster, all petals, lower surface: Smooth, glabrous; slightly glossy. Color, all petals: When opening and fully opened, upper surface: Darker and more intense than N57A and N66A; towards the base, close to 53A; color does not change with development. When opening and fully opened, lower surface: Close to N66A to N66B; towards the base, close to 53A; color does not change with development.

*Sepals*.—Quantity and arrangement: Three in a single whorl; two laterals are opposite and the third modified into an elongated spur. Lateral sepal length: About 1 cm. Lateral sepal width: About 6 mm. Lateral sepal shape: Ovate. Lateral sepal apex: Acute to acuminate. Lateral sepal base: Truncate. Lateral sepal margin: Entire, not undulate. Lateral sepal texture and luster, upper surface: Smooth, glabrous; moderately glossy. Lateral sepal texture and luster, lower surface: Smooth, glabrous; somewhat glossy. Lateral sepal color, upper surface: Close to 147C to 147D. Lateral sepal color, lower surface: Close to 147C to 147D tinged with close to 187C. Spur length: About 4.25 cm. Spur diameter: At flower, about 2 mm; at apex, less than 1 mm. Spur shape: Acicular, curved. Spur texture and luster: Smooth, glabrous; somewhat glossy. Spur color: Close to 59A.

*Peduncles*.—Length: About 4 cm. Diameter: About 2.5 mm. Angle: About 45° from vertical. Strength: Strong; flexible. Texture and luster: Smooth, glabrous; glossy. Color: Close to 59A.

*Reproductive organs*.—Stamens: Quantity: Five fused at anthers; filaments free. Filament length: About 4 mm. Filament color: Close to 158A. Anther length: About 2.5 mm. Anther shape: Oblong. Anther color: Close to N155B. Pollen amount: Moderate. Pollen color: Close to 158A. Pistils: Quantity per flower: One. Pistil length: About 5 mm. Stigma shape: Crested. Stigma color: Close to 144A. Style length: About 4 mm. Style color: Close to 144A. Ovary color: Close to 144A and 187A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongimagma' as illustrated and described.

* * * * *